(12) United States Patent
Nagashima

(10) Patent No.: US 6,617,461 B2
(45) Date of Patent: Sep. 9, 2003

(54) PROCESS FOR PREPARATION OF OPTICALLY ACTIVE N-SUBSTITUTED AZETIDINE-2-CARBOXYLIC ACIDS

(75) Inventor: Nobuo Nagashima, Takasago (JP)

(73) Assignee: Kaneka Corporation, Osaka (JP)

(*) Notice: Subject to any disclaimer, the term of this patent is extended or adjusted under 35 U.S.C. 154(b) by 0 days.

(21) Appl. No.: 09/926,189

(22) PCT Filed: Jan. 25, 2001

(86) PCT No.: PCT/JP01/00469

§ 371 (c)(1),
(2), (4) Date: Dec. 20, 2001

(87) PCT Pub. No.: WO01/55104

PCT Pub. Date: Aug. 2, 2001

(65) Prior Publication Data

US 2003/0045730 A1 Mar. 6, 2003

(30) Foreign Application Priority Data

Jan. 25, 2000 (JP) .......................... 2000-016346

(51) Int. Cl.⁷ ............................................... C07D 205/04
(52) U.S. Cl. ........................................................ 548/953
(58) Field of Search .................... 548/953; 560/161; 562/555, 556

(56) References Cited

U.S. PATENT DOCUMENTS 6,333,418 B1 * 12/2001 Parratt et al. ................ 548/953

FOREIGN PATENT DOCUMENTS

WO          98/35949 A1 * 8/1998

OTHER PUBLICATIONS

Higashi, K. et al, Chem. Pharm. Bull., 1986, 34, 4927–4932.*
Hoshi, Hideaki et al, J. Antibiotics, 1990, 43, 858–872.*
Streitwieser, A. and Heathcock, C.H., "Introduction to Organic Chemistry, 2nd Ed.", Macmillan, New York, 1981, p. 143.*

P. Hamilton; "Proline: Synthesis from Ornithine, Citrulline or Arginine"; Journal of Biol. Chem., vol. 198, pp. 587–597; 1952.

* cited by examiner

*Primary Examiner*—Richard L. Raymond
*Assistant Examiner*—Thomas McKenzie
(74) *Attorney, Agent, or Firm*—Armstrong, Westerman & Hattori, LLP

(57) ABSTRACT

The object of the present invention is to produce an optically active N-substituted azetidine-2-carboxylic acid by an efficient, expendient and commercially profitable process.

The present invention provides a production method of an optically active N-substituted azetidine-2-carboxyic acid represented by the general formula (2):

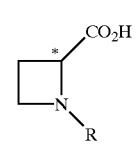

(2)

in the formula, R represents a substituted oxycarbonyl type protecting group or a substituted sulfonyl type protective group and * represents an asymmetric carbon atom which comprises cyclizing an optically active 4-substituted amino-2-halobutyric acid represented by the general formula (1):

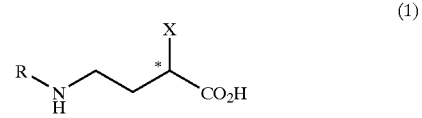

(1)

in the formula, R represents a substituted oxycarbonyl type protective group or a substituted sulfonyl type protective group, X represents a halogen atom and * represents an asymmetric carbon atom, in the presence of a base.

5 Claims, No Drawings

PROCESS FOR PREPARATION OF OPTICALLY ACTIVE N-SUBSTITUTED AZETIDINE-2-CARBOXYLIC ACIDS

TECHNICAL FIELD

The present invention relates to a process for producing optically active N-substituted azetidine-2-carboxylic acids of value as pharmaceutical intermediates, intermediate compounds of use in the above production, and a process for producing them.

BACKGROUND ART

The following processes are known for the production of optically active N-substituted azetidine-2-carboxylic acids.
(1) A process which comprises reacting a racemic di-substituted butyric acid ester with an optically active alkylbenzylamine to give a diastereomer pair of optically active N-(alkylbenzyl)azetidine-2-carboxylic acid esters and hydrolyzing the ester bond to give a diastereomer pair of optically active N-(alkylbenzyl)azetidine-2-carboxylic acids (JP 10-130231A).
(2) A process which comprises permitting an enzyme having asymmetrically hydrolyzing activity to act on an N-substituted azetidine-2-carboxylic acid ester to give a mixture of optically active N-substituted azetidine-2-carboxylic acid and optically active N-substituted azetidine-2-carboxylic acid ester and fractionating it into the respective compounds (JP 11-46784A)
(3) A process which comprises subjecting a racemic N-acylazetidine-2-carboxylic acid ester to enzymatic asymmetric hydrolysis to give a mixture of optically active N-acylazetidine-2-carboxylic acid and optically active N-acylazetidine-2-carboxylic acid ester and fractionating it into the respective compounds (WO 9802568).
(4) A process which comprises cyclizing an optically active N-substituted α-amino-γ-halobutyric acid ester derived from optically active methionine to give an optically active N-substituted azetidine-2-carboxylic acid ester and hydrolyzing the ester bond to give an optically active N-substituted azetidine-2-carboxylic acid (JP10-120648A).

However, the above processes have the following problems.

In the process (1), the stereoselectivity of the reaction is generally poor so that the diastereomer pair of optically active N-(alkylbenzyl)azetidine-2-carboxylic acid esters is heavily contaminated with unwanted stereoisomer. Therefore, in order to obtain the desired stereoisomer, it is necessary to separate a large amount of such unwanted isomer so that the process is not satisfactory enough in terms of efficiency and economics and can hardly be exploited for commercial production.

In the processes (2) and (3), both of which are optical resolution techniques utilizing an enzyme, the theoretical yield of the desired stereoisomer does not exceed 50% and, moreover, the remaining large amount of unwanted isomer must be separated, with the result that neither of these processes is satisfactory enough in efficiency and economics and that these processes have problems to be exploited for the commercial production.

In the process (4) wherein the starting compound having an ester group is cyclized for synthesizing an optically active N-substituted azetidine-2-carboxylic acid, a hydrolysis step is inevitably required for cleaving off the ester group from the optically active N-substituted azetidine-2-carboxylic acid ester obtained.

Thus, all of the conventional processes have inherent drawbacks in terms of efficiency and have problems to be solved as for the commercial production processes.

SUMMARY OF THE INVENTION

In the light of the above-mentioned circumstance, the inventor conducted an intensive research to provide an efficient, economical and commercially useful process for producing an optically active N-substituted azetidine-2-carboxylic acid, found that such an optically active N-substituted azetidine-2-carboxylic acid can be provided, expediently and easily, by cyclizing an optically active starting compound having a carboxy group and reached to the present invention.

DETAILED DESCRIPTION OF THE INVENTION

The present invention, therefore, provides a production method of an optically active N-substituted azetidine-2-carboxylic acid represented by the general formula (2):

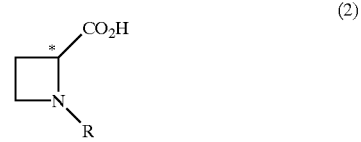

in the formula, R represents a substituted oxycarbonyl type protective group or a substituted sulfonyl type protective group and * represents an asymmetric carbon atom, which comprises cyclizing an optically active 4-substituted amino-2-halobutyric acid represented by the general formula (1):

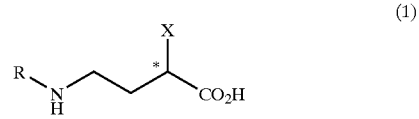

in the formula, R represents a substituted oxycarbonyl type protective group or a substituted sulfonyl type protective group, X represents a halogen atom and * represents an asymmetric carbon atom, in the presence of a base.

The present invention further provides a production method of an optically active 4-substituted amino-2-chlorobutyric acid represented by the general formula (3):

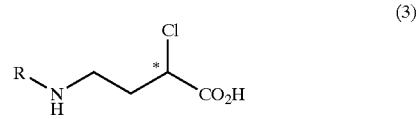

in the formula, R represents a substituted oxycarbonyl type protective group or a substituted sulfonyl type protective group and * represents an asymmetric carbon atom, which comprises subjecting an optically active 4-amino-2-chlorobutyric acid represented by the general formula (4):

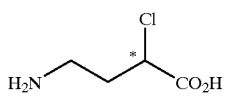

(4)

in the formula, * represents an asymmetric carbon atom, to amino group protection in the presence of a base.

The present invention further provides a novel compound, namely, an optically active 4-substituted amino-2-chlorobutyric acid represented by the general formula (3):

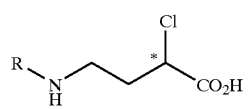

(3)

in the formula, R represents a substituted oxycarbonyl type protective group or a substituted sulfonyl type protective group and * represents an asymmetric carbon atom.

The present invention is now described in detail.

First, the optically active 4-substituted amino-2-halobutyric acid represented by the following general formula (1):

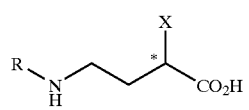

(1)

in the formula, R represents a substituted oxycarbonyl type protective group or a substituted sulfonyl type protective group, X represents a halogen atom and * represents an asymmetric carbon atom, for use in the present invention is described.

In this compound, the substituent R represents a substituted oxycarbonyl type protective group or a substituted sulfonyl type protective group. The substituted oxycarbonyl type protective group includes, for example, alkyloxycarbonyl groups which may be substituted, such as methoxycarbonyl, ethoxycarbonyl, 2,2,2-trichloroethoxycarbonyl, 2-trimethylsilylethoxycarbonyl, 2-phenylethoxycarbonyl, 1,1-dimethyl-2,2,2-trichloroethoxycarbonyl, tert-butoxycarbonyl, 1-adamantyloxycarbonyl, allyloxycarbonyl, cinnamyloxycarbonyl, 4-nitrocinnamyloxycarbonyl, 2-methylthioethoxycarbonyl, isobutyloxycarbonyl, tert-amyloxycarbonyl, cyclopentyloxycarbonyl, cyclohexyloxycarbonyl and 1-methylcyclohexyloxycarbonyl; and aralkyloxycarbonyl groups which may be substituted, such as 9-fluorenylmethyloxycarbonyl, benzyloxycarbonyl, 4-methoxybenzyloxycarbonyl, 4-nitrobenzyloxycarbonyl, 2-nitrobenzyloxycarbonyl, 4-chlorobenzyloxycarbonyl, 4-bromobenzyloxycarbonyl, 2,4-dichlorobenzyloxycarbonyl, 4-methylsulfinylbenzyloxycarbonyl, 3,5-dimethoxybenzyloxycarbonyl, 4-decyloxybenzyloxycarbonyl, 2,4,6-trimethylbenzyloxycarbonyl, diphenylmethyloxycarbonyl and 9-anthrylmethyloxycarbonyl. In consideration of commercial availability of the protective group-providing reagent and the ease of deprotection, benzyloxycarbonyl or tert-butoxycarbonyl is preferably used.

The substituted sulfonyl type protective group includes, for example, methanesulfonyl, 2-trimethylsilylethanesulfonyl, phenylmethanesulfonyl, trifluoromethanesulfonyl, benzenesulfonyl, p-toluenesulfonyl, 2-nitrobenzenesulfonyl, 4-nitrobenzenesulfonyl, 4-methoxybenzenesulfonyl, 2,4,6-trimethoxybenzenesulfonyl, 2,6-dimethyl-4-methoxybenzenesulfonyl, 2,4,6-trimethylbenzenesulfonyl, pentamethylbenzenesulfonyl and 9-anthracenesulfonyl. Among these, p-toluenesulfonyl, 2-nitrobenzenesulfonyl or 4-nitrobenzenesulfonyl can be used preferably.

Referring, further, to the compound represented by the general formula (1), X represents a halogen atom which may for example be a chlorine, a bromine, an iodine or a fluorine. However, in view of the reactivity in the subsequent stage of the production and of the racemization suppression, a chlorine or a bromine is preferred and a chlorine is most preferred. When X in the general formula (1) represents a chlorine, the optically active 4-substituted amino-2-chlorobutyric acid represented by the following general formula (3):

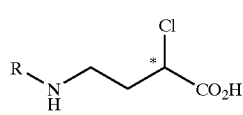

(3)

in the formula, R and * are as defined above, is a novel compound.

The compound represented by the general formula (1) is prepared by introducing a protective group R into the corresponding optically active 4-amino-2-halobutyric acid in the presence of a base. The starting compound, namely, the optically active 4-amino-2-halobutyric acid can be obtained by the known process. In the case of 4-amino-2-chlorobutyric acid, for example, Biochemical Journal 64, 323 (1956) describes a process for obtaining (S)-4-amino-2-chlorobutyric acid from (S)-2,4-diaminobutyric acid. Further, Japanese Patent Application Hei-11-169620 describes a process for obtaining (R)-4-amino-2-chlorobutyric acid by hydrolyzing (R)-4-amino-2-chlorobutyric acid methyl ester.

In the present invention, any configuration of the 4-amino-2-halobutyric acid may be used, but an (R)-4-amino-2-halobutyric acid is used for the production of an (S)-N-substituted azetidine-2-carboxylic acid which is important as an intermediate of medicinal substances. Moreover, the optically active 4-amino-2-halobutyric acid for use in the present invention may be a pure enantiomer of the (R)- or (S)-form or a mixture of the two enantiomers one of which accounts for a predominant proportion. However, it goes without saying that in order to obtain an optically active N-substituted azetidine-2-carboxylic acid of high optical purity, the use of the 4-amino-2-halobutyric acid of high optical purity is preferred.

The introduction reaction of the protective group R into said 4-amino-2-halobutyric acid can be carried out by the routine procedure described in the relevant books, for example, T. W. Greene, P. G. M. Wuts: Protective Groups In Organic Synthesis, Second Edition, John Wiley & Sons, Inc. For the introduction of a substituted oxycarbonyl type protective group, a substituted oxycarbonyl type protectant activated in the form of halide, active ester, anhydride, azide, cyanide or the like can be employed. For the introduction of a substituted sulfonyl type protective group, a substituted sulfonyl type protectant activated in the form of chloride, anhydride or the like can be employed.

As examples of said substituted oxycarbonyl type protectant, there can be mentioned, methyl chlorocarbonate, ethyl chlorocarbonate, 2,2,2-trichloroethyl chlorocarbonate, N-succinimidyl 2,2,2-trichloroethylcarbonate, 2-trimethylsilylethyl chlorocarbonate, N-succinimidyl 2-trimethylsilylethylcarbonate, 4-nitrophenyl 2-trimethylsilylethylcarbonate, 2-trimethylsilylethoxycarbonyl azide, 2-phenylethyl chlorocarbonate, di-tert-butyl dicarbonate, 1,2,2,2-tetrachloroethyl tert-butylcarbonate, tert-butoxycarbonyl azide, 1-adamantyl 2-pyridylcarbonate, diallyl dicarbonate, allyl benzotriazolylcarbonate, cinnamyl benzotriazolylcarbonate, 4-nitrocinnamyl chlorocarbonate, 9-fluorenylmethyl pentafluorophenylcarbonate, 9-fluorenylmethyloxycarbonyl azide, benzyl chlorocarbonate, dibenzyl dicarbonate, benzyl benzotriazolylcarbonate, benzyloxycarbonyl cyanide, 4-nitrobenzyl chlorocarbonate, 9-anthrylmethyl 4-nitrophenylcarbonate and diphenylmethyloxycarbonyl azide.

As examples of said substituted sulfonyl type protectant, there can be mentioned, methanesulfonyl chloride, 2-trimethylsilylethanesulfonyl chloride, phenylmethanesulfonyl chloride, trifluoromethanesulfonic anhydride, benzenesulfonyl chloride, p-toluenesulfonyl chloride, 2-nitrobenzenesulfonyl chloride, 4-nitrobenzenesulfonyl chloride, 4-methoxybenzenesulfonyl chloride, 2,4,6-trimethoxybenzenesulfonyl chloride, 2,6-dimethyl-4-methoxybenzenesulfonyl chloride, 2,4,6-trimethylbenzenesulfonyl chloride, pentamethylbenzenesulfonyl chloride and 9-anthracenesulfonyl chloride.

As the base for use in the introduction reaction of the protective group R, there can be mentioned organic tertiary amines such as triethylamine, diisopropylethylamine, pyridine, and the like; inorganic bases such as sodium carbonate, potassium carbonate, sodium hydrogen carbonate, sodium hydroxide, magnesium oxide, and the like; and organometallic bases such as n-butyllithium and so forth.

Further, a solvent is generally used in the above protective group-introducing reaction, the solvent to be used is not particularly restricted insofar as it does not interfere with the above protective group-introducing reaction. Thus, an organic solvent in general use, water, or a mixture of a hydrophilic organic solvent and water is preferably used. As examples of said solvents, there can be mentioned, the common solvents such as methylene chloride, chloroform, N,N-dimethylformamide, acetonitrile, dioxane, tetrahydrofuran, dimethoxyethane, tert-butyl alcohol and water-dioxane.

In the present invention, the optically active 4-substituted amino-2-halobutyric acid represented by the general formula (1), obtained as above, is cyclized in the presence of a base to give an optically active N-substituted azetidine-2-carboxylic acid represented by the following general formula (2):

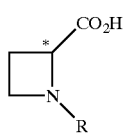

(2)

in the formula, R and * are as defined above. This cyclization is now described.

The cyclization reaction proceeds with the simultaneous inversion of the configuration on the carbon atom to which the halogen atom X in the compound represented by the general formula (1) is bonded. Thus, a (S)-N-substituted azetidine-2-carboxylic acid is obtained from a (R)-4-substituted amino-2-halobutyric acid, and similarly a (R)-N-substituted azetidine-2-carboxylic acid from a (S)-4-substituted amino-2-halobutyric acid.

In this cyclization reaction, the substituent R in the compound represented by the general formula (1) is not affected but becomes the substituent R in the compound represented by the general formula (2). Therefore, the substituent R in the compound represented by the general formula (2) has the same meaning as defined hereinbefore, i.e. the substituted oxycarbonyl type or the substituted sulfonyl type protective group, which has already been described in detail. In this connection, the preferred substituent R in the compound represented by the general formula (2) is tert-butoxycarbonyl, benzyloxycarbonyl, p-toluenesulfonyl, 2-nitrobenzenesulfonyl, or 4-nitrobenzenesulfonyl group.

The base to be used in the above cyclization reaction includes, for example, alkali metal hydrides such as lithium hydride, sodium hydride, potassium hydride and the like; alkali metal alcoholates such as lithium methoxide, sodium methoxide, sodium ethoxide, potassium tert-butoxide and the like; alkali metal hydroxides such as lithium hydroxide, sodium hydroxide, potassium hydroxide, cesium hydroxide and the like; alkali metal amides such as lithium amide, sodium amide, lithium diisopropylamide, lithium hexamethyldisilazide, sodium hexamethyldisilazide, potassium hexamethyldisilazide and the like; and organolithium compounds such as n-butyllithium, sec-butyllithium, tert-butyllithium, and so forth. Among these, alkali metal hydrides, alkali metal alcoholates and alkali metal hydroxides are preferred. Sodium hydride, sodium methoxide, potassium tert-butoxide and potassium hydroxide are used more preferably.

Further, its amount of use is not particularly restricted unless it is not less than 2 molar equivalents relative to the substrate compound represented by the general formula (1) but from economic considerations is preferably as close to 2 molar equivalents as possible. From the standpoint of rapid completion of the reaction, it is preferable to use an excess over 2 molar equivalents. The usual range is 2 to 10 molar equivalents and the preferred range is 2 to 4 molar equivalents.

Usually, a solvent is used in the above cyclization reaction. The solvent mentioned above includes, for example, ether solvents such as tetrahydrofuran, dioxane, ethyl ether, isopropyl ether, tert-butyl methyl ether, dimethoxyethane and the like; amide solvents such as N,N-dimethylformamide and the like; sulfoxide solvents such as dimethyl sulfoxide and the like; halogen solvents such as dichloromethane, dichloroethane, chloroform and the like; aromatic hydrocarbon solvents such as toluene, xylene and the like; and alcohol solvents such as methanol, ethanol, isopropyl alcohol, tert-butyl alcohol and so forth.

These solvents are used each independently or in combination with two or more of them and its amount of use is within the range of 10 to 50 volume parts based on the weight of the substrate compound represented by the general formula (1).

Where necessary, to accelerate the reaction, this reaction can also be carried out in the presence of a polyether type highly polar aprotic solvent, such as diethylene glycol dimethyl ether. In such cases, the amount of such highly polar aprotic solvent to be added is within the range of 0.5 to 2 molar equivalents relative to the substrate compound represented by the general formula (1).

For example, this cyclization reaction is carried out by mixing the substrate compound represented by the general formula (1) with the base in the solvent. Any of the following methods can be applied: the method which comprises adding a substrate solution in the solvent to the base, the method which comprises adding the base to the substrate solution in the solvent, and the method in which the substrate, the base and the solvent are mixed together in one step. The optimum method is preferably chosen with reference to the kind of the base to be used.

The cyclization reaction temperature depends on the kind of the base, the solvent and the substrate compound represented by the general formula (1) to be used but can generally be any arbitrary temperature from the freezing point to boiling point of the solvent to be used. To complete the reaction in a short period of time, the reaction is preferably carried out at an elevated temperature, while a low temperature is preferred for suppressing racemization during the reaction. The usual temperature range is 0 to 90° C.

The cyclization reaction period highly depends on conditions of the reaction and cannot be stated in general terms. Usually, however, by monitoring the reaction mixture periodically by the routine analytical technique, such as thin-layer chromatography (TLC), high performance liquid chromatography (HPLC), or gas chromatography (GLC), disappearance of the starting substrate compound can be detected to know the end point of the reaction and the reaction can be accordingly terminated.

The above cyclization reaction is followed by an operation to isolate the desired product optically active N-substituted azetidine-2-carboxylic acid compound represented by the general formula (2) from the reaction mixture. Generally, this isolation procedure should be varied more or less according to whether the reaction solvent used in the cyclization reaction is a water-soluble organic solvent or a water-insoluble organic solvent. Thus, when a water-soluble organic solvent is used, the water-soluble reaction solvent is preferably concentrated and distilled off before the extraction of the desired product. Although this concentration and distillation procedure for removal can be omitted when the extraction is to be carried out at a high dilution factor with a large volume of extraction solvent or water, such a practice would be undesirable from economic points of view. On the other hand, when a water-insoluble organic solvent is used, the extraction procedure of the desired product can be started without concentration and distillation for removal of the reaction solvent.

While there is such a minor variation as above, the reaction mixture can be generally treated as follows to isolate the desired product compound represented by the general formula (2). Thus, an organic acid or an inorganic acid is added in a suitable amount to the reaction mixture to neutralize the remaining base and to make free the carboxyl group of the product compound represented by the general formula (2) at the same time. For this purpose, the organic acid and the inorganic acid may be used in combination.

For example, after the used base is neutralized with the organic acid, the pH may be adjusted by the addition of the inorganic acid. The organic acid which can be used here includes, for example, organic carboxylic acids, such as formic acid, acetic acid and the like, and organic sulfonic acids, such as methanesulfonic acid, benzenesulfonic acid, toluenesulfonic acid and the like, with formic acid and acetic acid being preferred. As for said inorganic acid, there may be mentioned hydrochloric acid, sulfuric acid, phosphoric acid and perchloric acid. Usually these acids are put to use as diluted with water appropriately, and hydrochloric acid is particularly preferred.

The optimum amount of addition of such acid can be roughly estimated from the amount of the base used for the cyclization reaction. Usually, the acid is used in a small excess over the amount necessary to neutralize the base used completely and so as to make the pH of the water phase after neutralization about 1 to 2.

Then, where necessary, the reaction solvent is concentrated and distilled off and the desired compound is extracted by adding water and an extraction solvent. The solvent which can be used as the extraction solvent is not particularly restricted in so far as it is an organic solvent capable of dissolving the desired product compound represented by the general formula (2) to an appropriate extent and having a poor affinity for water. Usually, ethyl acetate is preferably used. The extract is dried, where necessary, and the concentrate obtained after removal of the solvent by distillation is purified by the routine purification method, such as silica gel chromatography or crystallization, whereby the optically active N-substituted azetidine-2-carboxylic acid compound represented by the general formula (2) can be isolated.

Furthermore, the present invention provides not only the above mode in which an optically active 4-substituted amino-2-halobutyric acid represented by the general formula (1) is cyclized in the presence of a base to give an optically active N-substituted azetidine-2-carboxylic acid represented by the general formula (2) but also a mode in which an optically active 4-amino-2-chlorobutyric acid represented by the general formula (4) is subjected to amino group protection in the presence of a base to give an optically active 4-substituted amino-2-chlorobutyric acid represented by the general formula (3) and, further, a mode of providing a novel optically active 4-substituted amino-2-chlorobutyric acid represented by the general formula (3).

Referring to the latter of the above two modes, it has already been pointed out in the foregoing description that the mode correspond to the case in which a halogen atom X of the compound represented by the general formula (1) is a chlorine and that the product is a novel compound. Moreover, the substituent R of the compound represented by the general formula (3) has the same meaning as the substituent R in the compound represented by the general formula (1). These aspects will not be described in any further detail. The particularly preferred substituent R in the compound represented by the general formula (3) in the invention is tert-butoxycarbonyl, benzyloxycarbonyl, p-toluenesulfonyl, 2-nitrobenzenesulfonyl or 4-nitrobenzenesulfonyl group.

Regarding the former mode, too, the optically active 4-amino-2-chlorobutyric acid represented by the general formula (4) can be converted to the compound represented by the general formula (3) by exactly the same method as that of obtaining the compound represented by the general formula (1) which has already been described herein before in detail and, therefore, this aspect is not described in any further detail.

BEST MODE FOR CARRYING OUT THE INVENTION

The following examples are further illustrative but by no means limitative of the present invention. It is to be noted that the optical purity values given were determined by high performance liquid chromatography.

REFERENCE EXAMPLE

In 100 ml of methanol was dissolved 12.28 g of (R)-4-amino-2-chlorobutyric acid methyl ester hydrochloride (optical purity 94.2% ee), followed by addition of 6.4 g of sulfuric acid under ice-cooling. The mixture was concentrated under reduced pressure and, with 50 ml of methanol added in the course, the concentration was further continued. The concentrate was dried under reduced pressure and 123 ml of water and 12.05 g of sulfuric acid were added. The mixture was stirred with heating on a warm water bath at 63 to 65° C. for 10 hours. During the reaction, the reaction mixture was brought under reduced pressure from time to time and the byproduct methanol was distilled off azeotropically with part of the water, while the reaction system was supplemented with the same volume of water as that removed. After completion of the heating, the reaction mixture was further stirred at room temperature for 62 hours and after confirming the disappearance of the starting compound by high-performance liquid chromatography (Develosil C30-UG-5 (Nomura Chemical)), the reaction was accordingly terminated. This aqueous solution was adjusted to pH 6.96 by adding sodium carbonate at room temperature, whereupon 168.39 g of an aqueous solution of (R)-4-amino-2-chlorobutyric acid was obtained (quantitative yield, optical purity 92.9% ee). The method used for optical purity analysis comprised concentrating said aqueous solution to dryness, converting the acid to the methyl ester with sulfuric acid-thionyl chloride-methanol, derivatizing it to (R)-3-chloro-2-pyrrolidinone with sodium hydrogen carbonate, and subjecting it to high performance liquid chromatography with a chiral column (Chiralcel OB-H (Daicel)).

Example 1

To 15.02 g of an aqueous solution of (R)-4-amino-2-chlorobutyric acid (optical purity 92.9% ee) as prepared in accordance with Reference Example was added 15 ml of tetrahydrofuran, and under ice-cooling and stirring, 1.86 g of sodium carbonate and 1.96 g of 2-nitrobenzenesulfonyl chloride were serially added. The mixture was stirred at room temperature for 42 hours, at the end of which time 12 ml of 3N hydrochloric acid was added. The mixture was then extracted 3 times with 30 ml portions of ethyl acetate. The organic layers were combined and dried over anhydrous sodium sulfate and the solvent was distilled off. The residue was purified by silica gel column chromatography (developer: methylene chloride/ethyl acetate=15/1~3/2) to give 1.32 g (yield 70.2%) of (R)-4-N-(2-nitrobenzenesulfonyl)amino-2-chlorobutyric acid.

$^1$H-NMR (CD$_3$OD) δ: 2.01~2.10 (m, 1H), 2.24~2.33 (m, 1H), 3.26 (dd, J=6.34, 7.32 Hz, 2H), 4.44 (dd, J=4.89, 8.79 Hz, 1H), 7.78~7.87 (m, 3H), 8.08~8.12 (m, 1H)

IR (KBr, cm$^{-1}$): 3325.7, 1720.7, 1537.5, 1371.6, 1350.3, 1174.8

Example 2

To 15.01 g of an aqueous solution of (R)-4-amino-2-chlorobutyric acid (optical purity 92.9% ee) as obtained in accordance with Reference Example was added 15 ml of tetrahydrofuran, and under ice-cooling and stirring, 0.96 g of sodium hydrogen carbonate and 1.66 g of p-toluenesulfonyl chloride were serially added. After 14 hours of stirring at room temperature, 5 ml of 3N hydrochloric acid was added and the mixture was extracted 3 times with 20 ml portions of ethyl acetate. The organic layers were combined and dried over anhydrous sodium sulfate and the solvent was distilled off. The residue was purified by silica gel column chromatography (developer: methylene chloride~methylene chloride/ethyl acetate=20/1~1/1) to give 1.12 g (yield 65.6%) of (R)-4-N-(p-toluenesulfonyl)amino-2-chlorobutyric acid.

$^1$H-NMR (CDCl$_3$) δ: 2.12~2.33 (m, 2H), 2.42 (s, 3H), 3.07~3.23 (m, 2H), 4.49 (dd, J=5.37, 7.33 Hz, 1H), 5.43 (s, 1H), 7.31 (d, J=8.3 Hz, 2H), 7.74 (d, J=8.3 Hz, 2H)

IR (KBr, cm$^{-1}$): 3283.2, 3254.3, 1716.9, 1419.8, 1329.1, 1317.5, 1306.0, 1292.5, 1159.4

Example 3

To 19.04 g of an aqueous solution of (R)-4-amino-2-chlorobutyric acid (optical purity 92.9% ee) as obtained in accordance with Reference Example was added 19 ml of tetrahydrofuran, and under ice-cooling and stirring, 2.41 g of sodium carbonate and 2.1 ml of benzyl chlorocarbonate were serially added. The mixture was stirred under ice-cooling for 30 minutes and further at room temperature for 22 hours. Then, 16 ml of 3N hydrochloric acid was added and the mixture was extracted 3 times with 40 ml portions of ethyl acetate. The organic layers were combined and dried over anhydrous sodium sulfate and the solvent was distilled off. The residue was purified by silica gel column chromatography (developer: methylene chloride/hexane=1/2~3/2~methylene chloride~methylene chloride/ethyl acetate=1/1) to give 1.39 g (yield 69.2%) of (R)-4-N-benzyloxycarbonylamino-2-chlorobutyric acid.

$^1$H-NMR (CDCl$_3$) δ: 2.10~2.40 (m, 2H), 3.34~3.48 (m, 2H), 4.42 (t, J=7.32 Hz, 1H), 5.10 (s, 1H), 5.40~6.10 (bs, 1H), 7.35 (s, 5H)

IR (CHCl$_3$, cm$^{-1}$): 3020.9, 1720.7, 1518.2, 1342.6, 1140.1

Example 4

To 344.79 g of an aqueous solution of (R)-4-amino-2-chlorobutyric acid (optical purity 89.4% ee) as obtained in accordance with Reference Example were added 12.34 g of sodium carbonate and a solution of 8.16 g of di-tert-butyl dicarbonate in 40 ml of tetrahydrofuran serially at room temperature with stirring. The mixture was stirred at room temperature for 19 hours, at the end of which time 100 ml of ethyl acetate was added. After phase separation, the aqueous layer was adjusted to pH 1.92 with 6N hydrochloric acid under ice-cooling. This solution was extracted 3 times with 100 ml portions of ethyl acetate and the organic layers were combined and dried over anhydrous sodium sulfate. The solvent was then distilled off and the residue was dried in vacuo to give 4.85 g (yield 70.3%) of (R)-4-N-(tert-butoxycarbonyl)amino-2-chlorobutyric acid.

$^1$H-NMR (CDCl$_3$) δ: 1.47 (s, 9H), 2.08~2.45 (bm, 2H), 3.25~3.45 (m, 2H), 4.35~4.50 (bs, 1H), 5.00~5.90 (bs, 1H)

IR (CHCl$_3$, cm$^{-1}$): 3020.9, 1716.9, 1508.5, 1369.6, 1167.1

Example 5

Under argon gas at room temperature, 333.8 mg of the (R)-4-N-(tert-butoxycarbonyl)amino-2-chlorobutyric acid obtained in Example 4 and dissolved in 8 ml of dry tetrahydrofuran was added dropwise to a suspension of 136.4 mg of 60% sodium hydride/oil in 2 ml of dry tetrahydrofuran under stirring and the reaction was conducted at room temperature for 23 hours and at 50° C. for 5 hours. To this reaction mixture under water cooling was added 0.2 ml of acetic acid and the solvent was distilled off. To the residue were added 15 ml of ethyl acetate, 15 ml of water, and 1.5 ml of 3N hydrochloric acid, and after phase separation, the aqueous layer was further extracted twice with the same amount of ethyl acetate. The organic layers were combined, dried over anhydrous sodium sulfate and filtered. The filtrate was sampled and analyzed by HPLC to confirm the formation of (S)-N-(tert-butoxycarbonyl)azetidine-2-carboxylic acid. The yield was 54.8%. The optical purity of the product as determined by high performance liquid chromatography with a chiral column (Chiralcel OD-R (Daicel)) was 89.5% ee and the optical yield over amino protection reaction through cyclization reaction was 100%. In addition, a sample of the product was purified by silica gel column chromatography and subjected to NMR analysis for the structural confirmation.

$^1$H-NMR (CDCl$_3$) δ: 1.48 (s, 9H), 2.40~2.60 (bs, 2H), 3.80~4.00 (bs, 2H), 4.80 (t, 1H)

Example 6

Under argon gas at room temperature, 333.6 mg of the (R)-4-N-(tert-butoxycarbonyl)amino-2-chlorobutyric acid obtained in Example 4 and dissolved in 8 ml of dry tetrahydrofuran was added dropwise to a suspension of 334.4 mg of potassium tert-butoxide in 2 ml of dry tetrahydrofuran under stirring and the reaction was conducted at room temperature for 43 hours. To this reaction mixture at room temperature was added 0.2 ml of acetic acid and the solvent was distilled off. To the residue were added 15 ml of ethyl acetate, 15 ml of water, and 1.5 ml of 3N hydrochloric acid, and after phase separation, the aqueous layer was further extracted twice with the same amount of ethyl acetate. The organic layers were combined, and dried over anhydrous sodium sulfate. The yield and optical purity were determined in the same manner as in Example 5. It was found that (S)-N-(tert-butoxycarbonyl)azetidine-2-carboxylic acid was obtained in a yield of 30.9% with an optical purity of 89.3% ee. The optical yield over amino protection reaction through cyclization reaction was 100%.

Example 7

To 345 mg of the (R)-4-N-(tert-butoxycarbonyl)amino-2-chlorobutyric acid obtained in Example 4 and dissolved in 7 ml of tert-butyl methyl ether was added 190.3 mg of 60% sodium hydride/oil in one operation at room temperature with stirring, immediately followed by argon purging. The reaction was carried out at room temperature for 30 minutes and further under reflux for 25 hours. This reaction mixture was ice-cooled and 0.15 ml of formic acid was added. Then, 15 ml of ethyl acetate, 15 ml of water and 1 ml of 3N hydrochloric acid were added and, after phase separation, the aqueous layer was further extracted twice with the same amount of ethyl acetate. The organic layers were combined and dried over anhydrous sodium sulfate and the solvent was distilled off. The residue was purified by silica gel column chromatography (developer: methylene chloride/hexane=1/1~methylene chloride~ethyl acetate) to give 0.25 g of oil. The yield and optical purity were determined as in Example 5. The analysis revealed the formation of (S)-N-(tert-butoxycarbonyl)azetidine-2-carboxylic acid in a yield of 31.4% with an optical purity of 86.7% ee. The optical yield over amino protection reaction through cyclization reaction was 97.0%. NMR analysis revealed that 23.7% of the starting compound remained intact.

Example 8

To a solution containing 547.9 mg of the (R)-4-N-(tert-butoxycarbonyl)amino-2-chlorobutyric acid obtained in Example 4 and 318 mg of diethylene glycol dimethyl ether in 11 ml of tert-butyl methyl ether was added 250.4 mg of 60% sodium hydride/oil in one operation under stirring at room temperature, immediately followed by argon purging. The reaction was carried out at room temperature for 30 minutes and further under reflux for 20 hours. This reaction mixture was cooled with ice and 0.25 ml of formic acid was added. Then, 25 ml of ethyl acetate, 25 ml of water and 1.6 ml of 3N hydrochloric acid were added and, after phase separation, the aqueous layer was further extracted twice with the same amount of ethyl acetate. The organic layers were combined and dried over anhydrous sodium sulfate and the solvent was distilled off. The residue was purified by silica gel column chromatography in the same manner as in Example 7 to give 0.46 g of oil. The yield and optical purity were determined in the same manner as in Example 5. The analysis revealed the formation of (S)-N-(tert-butoxycarbonyl)azetidine-2-carboxylic acid in a yield of 63.9% with an optical purity of 83.7% ee. The optical yield over amino protection reaction through cyclization reaction was 93.6%.

Example 9

A solution containing 325.9 mg of the (R)-4-N-(tert-butoxycarbonyl)amino-2-chlorobutyric acid obtained in Example 4 and 189 mg of potassium hydroxide in 7 ml of tert-butyl alcohol was reacted under reflux for 7 hours and the solvent was then distilled off. To the residue were added 15 ml of ethyl acetate, 15 ml of water and 1.8 ml of 3N hydrochloric acid, and after phase separation, the aqueous layer was further extracted twice with the same amount of ethyl acetate. The organic layers were combined and dried over anhydrous sodium sulfate and the solvent was distilled off to obtain 0.12 g of oil. The yield and optical purity were determined in the same manner as in Example 5. The analysis revealed the formation of (S)-N-(tert-butoxycarbonyl)azetidine-2-carboxylic acid in a yield of 32.6% with an optical purity of 72.5% ee. The optical yield over amino protection reaction through cyclization reaction was 81.1%.

Example 10

To 269.7 mg of the (R)-4-N-benzyloxycarbonylamino-2-chlorobutyric acid obtained in Example 3 and dissolved in 4.7 ml of dimethoxyethane was added 80.6 mg of 60% sodium hydride/oil in one operation under ice-cooling and stirring, immediately followed by argon purging. The reaction was carried out under ice-cooling for 3 hours and at room temperature for 16 hours. This reaction mixture was ice-cooled and 25 ml of ethyl acetate, 15 ml of water and 1 ml of 3N hydrochloric acid were added. After phase separation, the aqueous layer was further extracted twice with the same amount of ethyl acetate. The organic layers were combined and dried over anhydrous sodium sulfate and the solvent was distilled off. The residue was purified by silica gel column chromatography (developer: methylene chloride/hexane=2/1~methylene chloride~methylene chloride/ethyl acetate=10/1~5/2) to give 91 mg of (S)-N-benzyloxycarbonylazetidine-2-carboxylic acid (yield 39%). The optical purity as determined by high performance liquid chromatography with a chiral column (Chiralcel OD-R (Daicel)) was 87.1% ee and the optical yield over amino protection reaction through cyclization reaction was 93.7%.

$^1$H-NMR (CDCl$_3$) δ: 2.40~2.66 (bs, 2H), 4.01 (bt, J=7.82 Hz, 2H), 4.75~4.90 (bs, 1H), 5.16 (s, 2H), 7.35 (s, 5H)

Example 11

To a solution containing 281 mg of the (R)-4-N-benzyloxycarbonylamino-2-chlorobutyric acid obtained in Example 3 in 4 ml of N,N-dimethylformamide was added 86.2 mg of 60% sodium hydride/oil in one operation under ice-cooling and stirring, immediately followed by argon purging. The reaction was carried out under ice-cooling for 1 hour and further at room temperature for 4.5 hours. This reaction mixture was cooled with ice and 0.5 ml of 3N hydrochloric acid was added. The solvent was then distilled off and the residue was diluted with 25 ml of ethyl acetate and 15 ml of water. After phase separation, the aqueous layer was further extracted twice with the same amount of ethyl acetate. In the course of reextraction, 0.5 ml of 3N hydrochloric acid was added to the aqueous phase. The organic layers were combined and dried over anhydrous sodium sulfate and the solvent was distilled off. The residue was purified by silica gel column chromatography in the same manner as in Example 10 to give 67.2 mg (yield 21.6%) of (S)-N-benzyloxycarbonylazetidine-2-carboxylic acid. The optical purity of the product as determined in the same manner as in Example 10 was 90.0% ee and the optical yield over amino protection reaction through cyclization reaction was 96.8%.

Example 12

To 234 mg of the (R)-4-N-(2-nitrobenzenesulfonyl)-amino-2-chlorobutyric acid obtained in Example 1 and dissolved in 4 ml of dimethoxyethane was added 62.3 mg of 60% sodium hydride/oil in one operation under ice-cooling and stirring, immediately followed by argon purging. The reaction was then conducted under ice-cooling for 1 hour and further at 50° C. for 23 hours. This reaction mixture was ice-cooled and 25 ml of ethyl acetate, 15 ml of water and 1 ml of 3N hydrochloric acid were added. After phase separation, the aqueous layer was further extracted twice with the same amount of ethyl acetate. The organic layers were combined and dried over anhydrous sodium sulfate and the solvent was distilled off. The residue was purified by silica gel column chromatography (developer: methylene chloride~methylene chloride/ethyl acetate=2/1) to give 156.6 mg of a mixture of the starting compound (6.4% recovery) and (S)-N-(2-nitrobenzenesulfonyl)azetidine-2-carboxylic acid (yield 67.8%). The ratio of the starting compound to the cyclization product compound was determined by NMR analysis. The optical purity of the product as determined by HPLC with a chiral column (Chiralcel OD-R (Daicel)) was 52.0% ee and the optical yield over amino protection reaction through cyclization reaction was 56.0%.

$^1$H-NMR (DMSO-d6) δ: 2.19~2.49 (m, 2H), 3.80~3.88 (m, 1H), 3.97~4.07 (m, 1H), 4.83 (dd, J=7.26, 9.57 Hz, 1H), 7.86~7.96 (m, 2H), 7.98~8.03 (m, 1H), 8.06~8.11 (m, 1H)

Example 13

To 162.8 mg of the (R)-4-N-(p-toluene-sulfonyl)amino-2-chlorobutyric acid obtained in Example 2 and dissolved in 4 ml of dimethoxyethane was added 49.4 mg of 60% sodium hydride/oil in one operation under ice-cooling and stirring, immediately followed by argon purging. The reaction was carried out under ice-cooling for 30 minutes, at room temperature for 8 hours, at 35° C. for 23 hours, and further at 50° C. for 40 hours. To this reaction mixture were added 25 ml of ethyl acetate, 10 ml of water and 1 ml of 3N hydrochloric acid at room temperature, and after phase separation, the aqueous layer was further extracted twice with the same amount of ethyl acetate. The organic layers were combined and dried over anhydrous sodium sulfate and the solvent was distilled off. The residue was purified by silica gel column chromatography (developer: methylene chloride/hexane=1/1~methylene chloride~methylene chloride/ethyl acetate=2/1) to give 137.9 mg of a mixture of the starting compound (25.4% recovery) and (S)-N-(p-toluenesulfonyl)azetidine-2-carboxylic acid (yield 67.8%). The ratio of the recovered starting compound to the cyclization product compound was determined by NMR analysis. The optical purity as determined by high performance liquid chromatography with a chiral column (Chiralcel OD-R (Daicel)) was 92.3% ee and the optical yield over amino protection reaction through cyclization reaction was 99.4%.

$^1$H-NMR (CDCl$_3$) δ: 2.24~2.33 (m, 1H), 2.43~2.56 (m, 1H), 2.49 (s, 3H), 3.65~3.79 (m, 2H), 4.49 (dd, J=7.81, 9.27 Hz, 1H), 7.42 (d, J=7.81 Hz, 2H), 7.76 (d, J=8.3 Hz, 2H)

Example 14

Under argon gas, 0.22 ml of 28% sodium methoxide/methanol was added to a solution containing 150.6 mg of the (R)-4-N-(p-toluenesulfonyl)amino-2-chlorobutyric acid obtained in Example 2 in 3 ml of dimethoxyethane with stirring under ice-cooling. The reaction was conducted under ice-cooling for 30 minutes, at room temperature for 10 hours, and further at 50° C. for 17 hours. Then, 25 ml of ethyl acetate, 10 ml of water and 1 ml of 3N hydrochloric acid were added to the reaction mixture at room temperature and, after phase separation, the aqueous layer was further extracted twice with the same amount of ethyl acetate. The organic layers were combined and dried over anhydrous sodium sulfate and the solvent was distilled off. The residue was purified by silica gel column chromatography in the same manner as in Example 13 to give 138 mg of a mixture of the starting compound (63.4% recovery) and (S)-N-(p-toluenesulfonyl)azetidine-2-carboxylic acid (yield 31.7%). The ratio of the recovered starting compound to the cyclization product compound was determined by NMR analysis as in Example 13. The optical purity as determined by high performance liquid chromatography was 86.0% ee and the optical yield over amino protection reaction through cyclization reaction was 92.6%.

INDUSTRIAL APPLICABILITY

In accordance to the present invention which is constituted as above, an optically active N-substituted azetidine-2-carboxylic acid can be produced from an optically active 4-substituted amino-2-halobutyric acid by a cyclization reaction with high efficiency, expediently, and profitably on a commercial scale.

What is claimed is:
1. A production method of an optically active N-substituted azetidine-2-carboxylic acid represented by the formula (2):

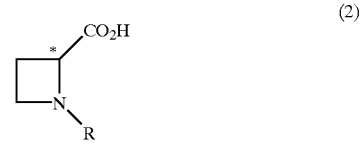

(2)

in the formula, R represents a substituted oxycarbonyl protective group or a substituted sulfonyl protective group and * represents an asymmetric carbon atom, which comprises cyclizing an optically active 4-substituted amino-2-halobutyric acid represented by the formula (1):

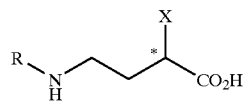
(1)

in the formula, R represents a substituted oxycarbonyl protective group or a substituted sulfonyl protective group, X represents a halogen atom and * represents an asymmetric carbon atom, in the presence of a base.

2. The production method according to claim 1, wherein the substituent R is tert-butoxycarbonyl, benzyloxycarbonyl, p-toluenesulfonyl, 2-nitrobenzenesulfonyl or 4-nitrobenzenesulfonyl group.

3. The production method according to claim 1 or 2, wherein the halogen atom X is a chlorine.

4. The production method according to claim 1 or 2, wherein the base is an alkali metal hydride, an alkali metal alcoholate or an alkali metal hydroxide.

5. The production method according to claim 4, wherein the base is sodium hydride, potassium tert-butoxide, sodium methoxide or potassium hydroxide.

* * * * *